United States Patent
Thao et al.

(10) Patent No.: US 7,819,870 B2
(45) Date of Patent: Oct. 26, 2010

(54) TISSUE CONTACT AND THERMAL ASSESSMENT FOR BRUSH ELECTRODES

(75) Inventors: Chou Thao, Brooklyn Park, MN (US); Hong Cao, Savage, MN (US); Saurav Paul, Minnetonka, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 760 days.

(21) Appl. No.: 11/617,397

(22) Filed: Dec. 28, 2006

(65) Prior Publication Data

US 2007/0106291 A1    May 10, 2007

Related U.S. Application Data

(63) Continuation-in-part of application No. 11/553,965, filed on Oct. 27, 2006, application No. 11/617,397, which is a continuation-in-part of application No. 11/549,100, filed on Oct. 12, 2006.

(60) Provisional application No. 60/730,634, filed on Oct. 27, 2005, provisional application No. 60/727,164, filed on Oct. 13, 2005.

(51) Int. Cl.
*A61B 18/18* (2006.01)

(52) U.S. Cl. ........................................ 606/41

(58) Field of Classification Search .............. 606/41–48
See application file for complete search history.

(56) References Cited

U.S. PATENT DOCUMENTS 4,682,596 A    7/1987    Bales et al.
4,799,495 A    1/1989    Hawkins et al.
4,911,174 A    3/1990    Pederson et al.

(Continued)

FOREIGN PATENT DOCUMENTS

EP    1491139    12/2004

(Continued)

OTHER PUBLICATIONS

Olaf J. Eick, et al., "The LETR-Principle: A Novel Method to Assess Electrode-Tissue Contact in Radiofrequency Ablation," Jul. 1998.

(Continued)

*Primary Examiner*—Linda C Dvorak
*Assistant Examiner*—Benjamin Lee
(74) *Attorney, Agent, or Firm*—Trenner Law Firm LLC

(57) ABSTRACT

System and methods are disclosed for tissue contact and thermal assessment, e.g. for tissue ablation procedures. An exemplary brush electrode comprises a plurality of flexible filaments adapted to transfer electrical energy to a tissue. At least one piezoelectric sensor is embedded among the plurality of flexible filaments. The at least one piezoelectric sensor is responsive to contact stress of the flexible filaments by generating electrical signals corresponding to the amount of contact stress. An output device is electrically connected to the at least one piezoelectric sensor. The output device receives the electrical signal for assessing tissue contact by the flexible filaments. The brush electrode may further comprise a sensing device mounted adjacent the at least one piezoelectric sensor, wherein the sensing device is a pressure sensor, a thermistor, a thermocouple, or an ultrasound sensor.

21 Claims, 9 Drawing Sheets

U.S. PATENT DOCUMENTS

| | | | |
|---|---|---|---|
| 4,976,711 A | 12/1990 | Parins et al. | |
| 5,028,394 A | 7/1991 | Lowell, Jr. et al. | |
| 5,341,807 A | 8/1994 | Nardella | |
| 5,354,279 A | 10/1994 | Hofling | |
| 5,372,603 A | 12/1994 | Acker et al. | |
| 5,405,346 A | 4/1995 | Grundy et al. | |
| 5,447,529 A | 9/1995 | Marchlinski | |
| 5,536,245 A | 7/1996 | Dahlbeck | |
| 5,643,197 A | 7/1997 | Brucker et al. | |
| 5,697,925 A | 12/1997 | Taylor | |
| 5,782,828 A | 7/1998 | Chen et al. | |
| 5,836,990 A | 11/1998 | Li | |
| 5,868,737 A | 2/1999 | Taylor et al. | |
| 5,893,848 A | 4/1999 | Negus et al. | |
| 5,895,355 A | 4/1999 | Schaer | |
| 5,947,905 A | 9/1999 | Hadjicostis et al. | |
| 6,013,074 A | 1/2000 | Taylor | |
| 6,039,731 A | 3/2000 | Taylor et al. | |
| 6,066,139 A | 5/2000 | Ryan et al. | |
| 6,078,830 A | 6/2000 | Levin et al. | |
| 6,113,592 A | 9/2000 | Taylor | |
| 6,113,593 A | 9/2000 | Tu et al. | |
| 6,127,672 A * | 10/2000 | Danisch | 250/227.14 |
| 6,171,304 B1 | 1/2001 | Netherly et al. | |
| 6,210,406 B1 | 4/2001 | Webster | |
| 6,217,573 B1 | 4/2001 | Webster | |
| 6,217,574 B1 | 4/2001 | Webster | |
| 6,241,724 B1 * | 6/2001 | Fleischman et al. | 606/41 |
| 6,246,898 B1 | 6/2001 | Vesely et al. | |
| 6,264,653 B1 | 7/2001 | Falwell | |
| 6,272,371 B1 | 8/2001 | Shlomo | |
| 6,304,776 B1 | 10/2001 | Muntermann | |
| 6,322,558 B1 | 11/2001 | Taylor et al. | |
| 6,325,799 B1 | 12/2001 | Goble | |
| 6,391,024 B1 | 5/2002 | Sun et al. | |
| 6,423,057 B1 | 7/2002 | He et al. | |
| 6,470,236 B2 | 10/2002 | Ohtsuki | |
| 6,696,844 B2 | 2/2004 | Wong et al. | |
| 6,800,986 B2 * | 10/2004 | Yamauchi | 310/348 |
| 6,837,886 B2 | 1/2005 | Collins et al. | |
| 6,845,264 B1 | 1/2005 | Skladnev et al. | |
| 6,882,885 B2 | 4/2005 | Levey, Jr. et al. | |
| 7,011,410 B2 * | 3/2006 | Bolger et al. | 351/209 |
| 7,060,965 B2 | 6/2006 | Vidovic et al. | |
| 2002/0123749 A1 | 9/2002 | Jain | |
| 2003/0056351 A1 * | 3/2003 | Wilkie et al. | 29/25.35 |
| 2003/0204184 A1 | 10/2003 | Ferek-Patric | |
| 2004/0199156 A1 | 10/2004 | Rioux et al. | |
| 2004/0210214 A1 * | 10/2004 | Knowlton | 606/41 |
| 2004/0217674 A1 * | 11/2004 | Bianchini | 310/365 |
| 2005/0159739 A1 | 7/2005 | Paul et al. | |
| 2005/0159741 A1 * | 7/2005 | Paul et al. | 606/41 |
| 2005/0267467 A1 | 12/2005 | Paul et al. | |
| 2007/0078484 A1 | 4/2007 | Talarico et al. | |
| 2008/0275442 A1 | 11/2008 | Paul et al. | |
| 2009/0158852 A1 | 6/2009 | Paul et al. | |

FOREIGN PATENT DOCUMENTS

WO     WO2005039835     5/2005

OTHER PUBLICATIONS

Measurement Specialties, Inc., "Piezo Film Sensors Technical Manual," Apr. 1999.

PCT International Search Report and Written Opinion of the International Searching Authority for PCT/US07/80981, dated Apr. 16, 2008, 9 pages.

PCT International Search Report and Written Opinion of the International Searching Authority for PCT/US07/80983 dated Apr. 2, 2008, 8 pages.

Biopac Systems, Inc., "Micro Pressure Measurement System—Product Overview," 39 pages.

"Fiber Optic Interferometer Fabry-Perot," available from http://physics.nad.ru/Physics/English/ifp_txt.htm at least as early as Oct. 15, 2007, 5 pages.

Medical Product Manufacturing News "Need to Know," 1 page, Sep. 2007.

BIOSEB: Samba—Blood Pressure System, available from http://www.bioseb.com/anglais/default/item_id=904_cat_id=3+Samba%20-%20Blood%20Pressure%System.php at least as early as Oct. 15, 2007, 4 pages.

Samba Sensors, "The Samba Technology," available from http://www.samba.se/index2.cfm?PageID=45 at least as early as Oct. 15, 2007, 1 page.

Samba Sensors, "Publications related to Samba Sensors AB," 3 pages.

PCT International Search Report and Written Opinion of the International Searching Authority for PCT/US06/39881, dated Jun. 30, 2008, 7 pages.

PCT International Search Report and Written Opinion of the International Searching Authority for PCT/US06/42119, dated Sep. 13, 2007, 9 pages.

* cited by examiner

TISSUE CONTACT AND THERMAL ASSESSMENT FOR BRUSH ELECTRODES

CROSS-REFERENCE TO RELATED APPLICATIONS

This application is a continuation-in-part of U.S. application Ser. No. 11/553,965 (filed 27 Oct. 2006), which claims the benefit of U.S. provisional application No. 60/730,634 (filed 27 Oct. 2005). This application is also a continuation-in-part of U.S. application Ser. No. 11/549,100 (filed 12 Oct. 2006), which claims the benefit of U.S. provisional application No. 60/727,164 (filed 13 Oct. 2005). Each of these applications is hereby incorporated by reference as though fully set forth herein.

BACKGROUND OF THE INVENTION a. Field of the Invention

The instant invention is directed toward a brush electrode and a method for using the brush electrode for tissue contact and thermal assessment, e.g., during ablation procedures. In particular, the brush electrode of the present invention comprises a plurality of flexible filaments or bristles which may be used for applying ablative energy (e.g., RF energy) to tissue during the formation of spot or continuous linear lesion, and means for tissue contact and thermal assessment during these procedures.

b. Background Art

It is well known that benefits may be gained by forming lesions in tissue if the depth and location of the lesion being formed can be controlled. In particular, it can be desirable to elevate tissue temperature to around 50° C. until lesions are formed via coagulation necrosis, which changes the electrical properties of the tissue. For example, when good or sufficiently deep lesions are formed at specific locations in cardiac tissue via coagulation necrosis, undesirable atrial fibrillations may be lessened or eliminated. The definition of "good" or "sufficiently deep" lesions depends at least to some extend on the procedure and may also depend on other considerations, such as tissue characteristics.

Several difficulties may be encountered, however, when attempting to form these lesions at specific locations using some existing ablation electrodes. For example, when forming lesions with RF energy, high temperature gradients are often encountered in the vicinity of the electrode. These high temperature gradients may result in the formation of undesirable coagulum and charring of the surface tissue. For example, undesirable coagulum may begin to form when blood reaches about 80° C. for an appreciable length of time, and undesirable tissue charring and desiccation may be seen when tissue reaches around 100° C. for an appreciable length of time. There are two types of undesirable coagulum. Coagulum may adhere to and damage the medical device itself. In addition, coagulum blood clots or curds may enter a patient's bloodstream, possibly resulting in other health problems for the patient. Charring of the surface tissue may also have deleterious effects on a patient.

As the temperature of the electrode is increased, the contact time required to form the lesions decreases, but the likelihood of charring surface tissue and forming undesirable coagulum increases. As the temperature of the electrode is decreased, the contact time required to form the lesions increases, but the likelihood of charring surface tissue and forming undesirable coagulum decreases. It is, therefore, a balancing act trying to ensure that tissue temperatures are adequately high for long enough to create good or sufficiently deep lesions, while still preventing or minimizing coagulum formation and/or charring of the surface tissue.

Thus, there remains a need for thermal assessment during ablation procedures.

Another difficulty encountered with existing ablation electrodes is ensuring adequate tissue contact. Maintaining adequate tissue contact for forming continuous linear lesions is not always readily determined using conventional fluoroscopy techniques. Instead, the physician determines tissue contact based on his/her experience maneuvering the electrode during the ablation procedure. Such experience only comes with time, and may be quickly lost if the physician does not use the electrode for ablation procedures on a regular basis. When used inside the heart, the beating heart further complicates matters by making it difficult to assess and maintain sufficient contact with the tissue for a sufficient length of time to form a desired lesion. If the contact between the electrode and the tissue cannot be properly maintained, a quality lesion is unlikely to be formed.

Thus there remains a need for tissue contact assessment during ablation procedures.

BRIEF SUMMARY OF THE INVENTION

It is desirable to be able to form adequately-deep or spot or continuous linear lesions in tissue while applying a reasonable amount of RF energy. This can be accomplished by assessing temperature to reduce the formation of undesirable coagulum and charring of the surface tissue. This can also be accomplished by assessing tissue contact to mitigating tissue contact problems during the procedure.

The present invention may be implemented in a brush electrode that facilitates tissue contact assessment during a medical procedure (e.g., ablation procedures). Optionally, the brush electrode may also be implemented for thermal assessment during these procedures. The brush electrode comprises a plurality of flexible filaments having longitudinal axes adapted to transfer ablative energy to tissue. The brush electrode also comprises a primary conductor operatively connected to, and adapted to transfer ablative energy to, the flexible filaments. Interstitial spaces are defined among the flexible filaments. In an exemplary embodiments where the brush electrode is a wet-brush electrode, the interstitial spaces are adapted to direct conductive fluid predominantly parallel to the longitudinal axes of the flexible filaments.

The brush electrode may comprise at least one piezoelectric sensor responds to contact and/or movement of the flexible filaments on a tissue by generating electrical signals indicative of tissue contact. The brush electrode may also comprise at least sensing device (e.g., pressure, thermistor, thermocouple, ultrasound sensor) to provide additional feedback to the user.

Output may be conveyed to the user in real-time (e.g., at a display device or other interface) so that the user can properly position the brush electrode on the tissue with the desired level of contact for the procedure. For example, the user may increase/reduce contact pressure if the output indicates insufficient/excessive contact for the procedure. Or for example, the user may increase/reduce the temperature if the output indicates insufficient/excessive temperature for the procedure.

In an exemplary embodiment, a brush electrode for tissue contact assessment comprises a plurality of flexible filaments adapted to transfer electrical energy to tissue. At least one piezoelectric sensor is embedded among the plurality of flexible filaments. The at least one piezoelectric sensor is responsive to contact stress of the flexible filaments by generating electrical signals corresponding to the amount of contact stress. An output device is electrically connected to the at least one piezoelectric sensor. The output device receives the electrical signals for assessing tissue contact by the flexible filaments. The brush electrode may further comprise a sensing device mounted adjacent the at least one piezoelectric sensor, wherein the sensing device may be a thermistor, a thermocouple, a pressure sensor, an ultrasound sensor, etc.

The present invention also comprises a method comprising: providing an exposed portion of a brush electrode for positioning adjacent to a tissue, generating piezoelectric signals in response to stress caused by an exposed portion of the brush electrode contacting the tissue, and outputting piezoelectric signals for assessing tissue contact. The method may further comprise generating output corresponding to a condition detected at the exposed portion of the brush electrode (e.g., a temperature condition).

The foregoing and other aspects, features, details, utilities, and advantages of the present invention will be apparent from reading the following description and claims, and from reviewing the accompanying drawings.

BRIEF DESCRIPTION OF THE DRAWINGS

FIG 1b is a cross-sectional view of the brush electrode taken along lines 1b-1b in FIG. 1a.

In FIG. 2a-b, the piezoelectric sensor is shown in exaggerated form as it may respond to various stresses, wherein FIG. 2a is a side-view piezoelectric sensor shown in FIG. 2, and FIG 2b is a top-view of the piezoelectric sensor shown in FIG. 2.

FIG. 6b is a cross-sectional view of the brush electrode taken along lines 6b-6b in FIG. 6a.

DETAILED DESCRIPTION OF THE INVENTION

Several embodiments of a brush electrode according to the present invention are depicted in the figures as the brush electrode may be use for tissue contact and thermal assessment during a medical procedure (e.g., an ablation procedure). As described further below, the brush electrode of the present invention provides a number of advantages, including, for example, the ability to control tissue contact and temperature during lesion formation in tissue to reduce or altogether eliminated the formation of undesirable coagulum and charring of the surface tissue. The brush electrode facilitates lesion formation in a shorter period of time than required by other ablation devices. The brush electrode also facilitates lesion formation in difficult environments (e.g., during ablation inside a beating heart), whether creating a spot lesion or a continuous linear lesion.

Before continuing, it is noted that other components typical of systems which are conventionally implemented for such procedures, are not shown or described herein for purposes of brevity. Such components may nevertheless also be provided as part of, or for use with, the brush electrode. For example, brush electrodes commonly include or are used in conjunction with an ECG recording system, an RF generator, and/or various input and output devices. Such components are well understood in the medical devices arts and therefore further explanation is not necessary for a complete understanding of the invention.

Figure 1:
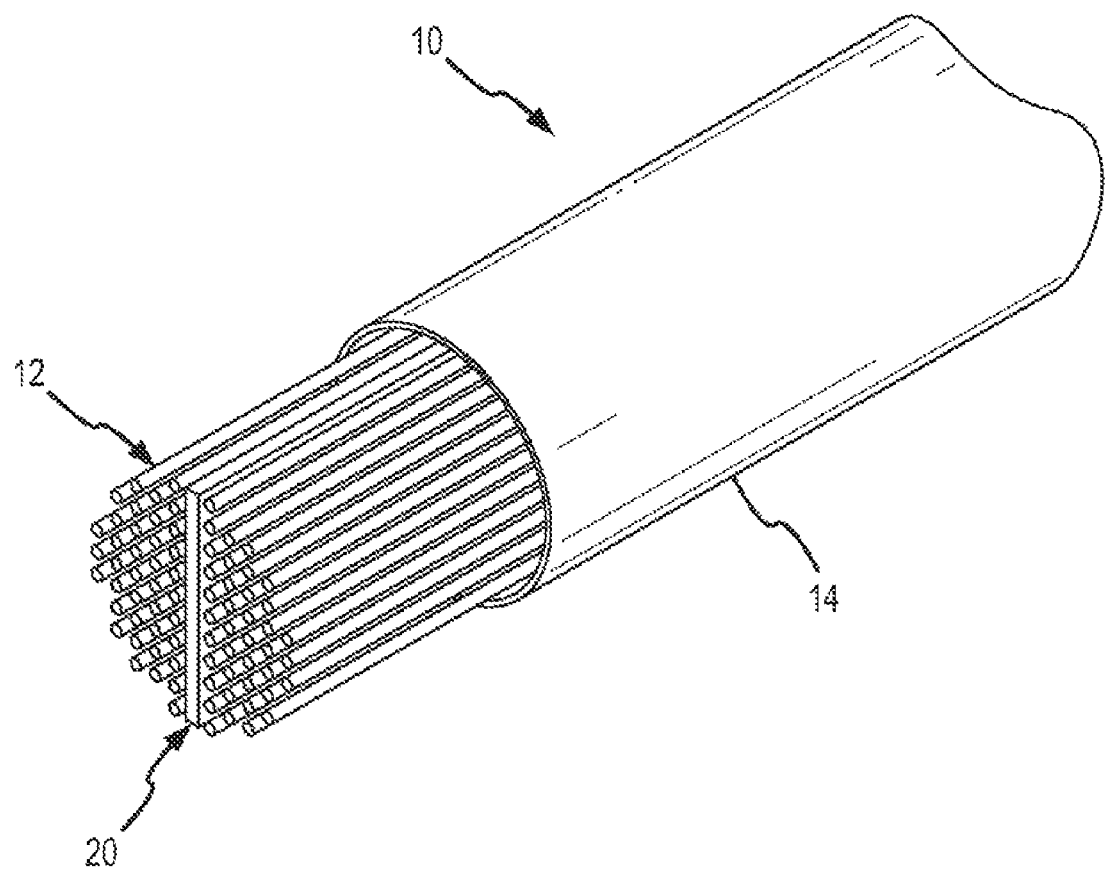
FIG. 1 is a perspective view of an exemplary embodiment of a brush electrode having a plurality of flexible filaments, and depicts a piezoelectric sensor embedded among the flexible filaments.
Figure 1A:
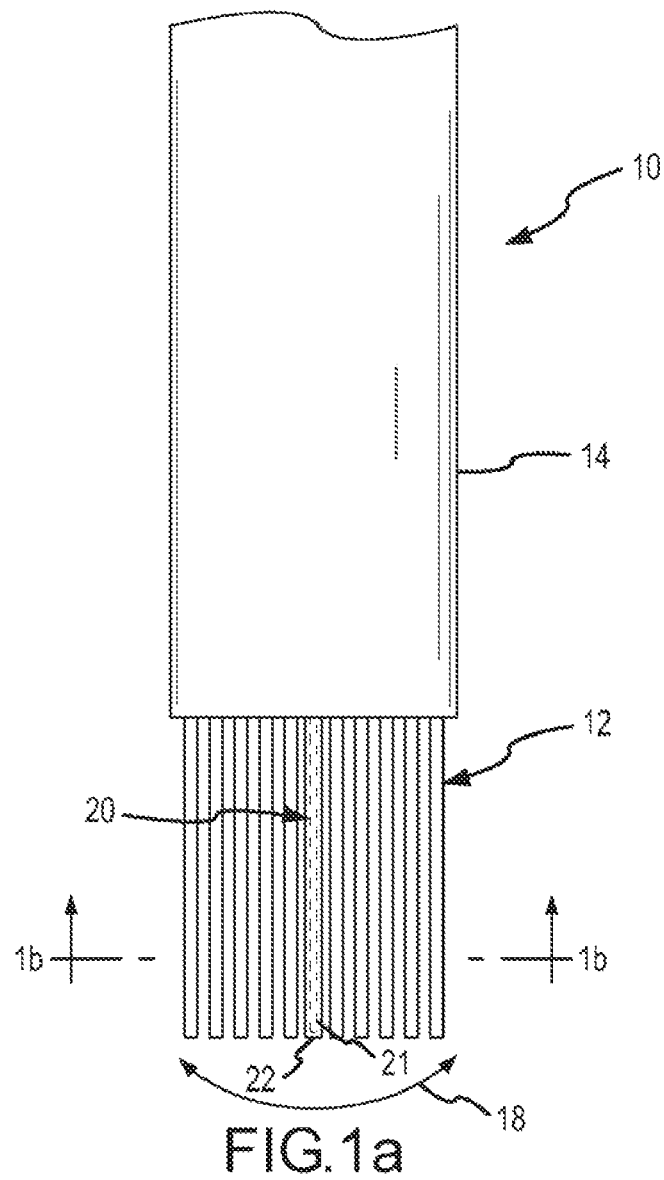
FIG. 1a is a side view of the brush electrode shown in FIG. 1.
Figure 1B:
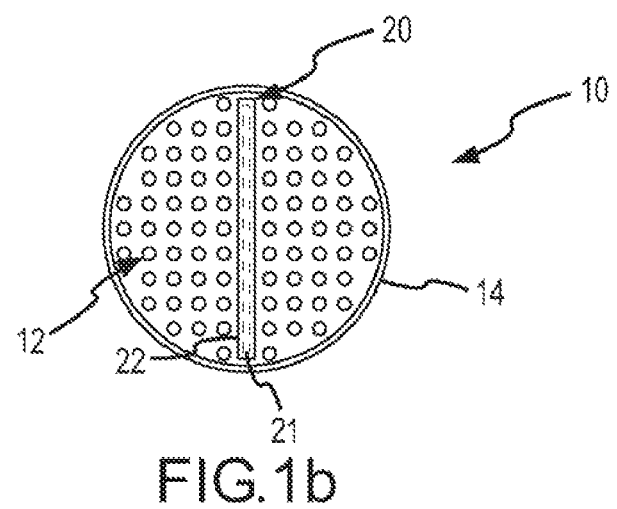

FIG. 1 is a perspective view of an exemplary embodiment of a brush electrode 10 having a plurality of flexible filaments 12 extending from a distal end of an outer sheath 14 of the brush electrode 10, and depicts a piezoelectric sensor 20 embedded among the flexible filaments 12. FIG. 1a is a side view of the brush electrode 10 shown in FIG. 1. FIG. 1b is a cross-sectional view of the brush electrode 10 taken along lines 1b-1b in FIG. 1a.

In an exemplary embodiment, the brush electrode 10 is comprised of about 2000 flexible filaments 12. The outer sheath 14 of the brush electrode 10 provides mechanical support for the flexible filaments 12 and may also provide electrical shielding. The flexible filaments 12 may project a few millimeters from the distal end of the outer sheath 14 of the brush electrode 10. It is noted that the number of flexible filaments 12 and the distance these extend from the outer sheath 14 may vary depending upon a number of factors including the composition of the flexible filaments 12 and the procedure for which the brush electrode 10 is to be used.

In an exemplary embodiment, the flexible filaments 12 may be made of a Nitinol fiber, and each of the flexible filaments has a diameter of approximately a 37 μm. It is noted, however, that size flexible filaments 12 of any suitable size may be used, and the flexible filaments 12 may be constructive from any of a wide variety of different types of materials, including nonconductive materials, semi-conductive materials, and conductive materials. Other exemplary materials include, but are not limited to metal fibers, metal plated fibers, carbon-compound fibers, acrylic fibers, and nylon fibers.

Optionally, the fibers may be coated with the conductive or nonconductive material. In addition, the flexible filaments 12 may be insulated from each other, or they may be in electrical contact with each other, and conductive or nonconductive fluids may flow through the filaments 12 or along the outer surface of the filaments 12. The electrical conductivity of the individual filaments may be constant along the length of the filaments or may vary along the length of the filaments. Also, if the conductivity of a filament varies along its length, it may vary continuously or discontinuously.

Although the flexible filaments 12 are depicted as having circular cross-sections, it is noted that the flexible filaments 12 may intentionally or unintentionally have a wide variety of cross-sectional configurations and area, and need not be circular. For example, manufacturing irregularities may result in flexible filaments 12 that have a variety of different cross-sectional configurations. Or for example, the flexible filaments 12 may be intentionally selected to have a variety of different cross-sectional configurations to achieve desired electrical properties. It is also note that while the flexible filaments 12 are depicted as substantially-parallel, longitudinally-extending fibers, in other embodiments the flexible filaments may comprise braided or twisted groups of fibers.

The particular types and configuration of flexible filaments 12 used for the brush electrode 10 will depend at least to some extend on design considerations. Exemplary design considerations may include, but are not limited to, the material and structural properties of individual filaments (e.g., what material(s) each individual filament is constructed from, whether the filaments are hollow or solid, whether the filaments are porous, and how flexible or stiff the filaments are), the length, shape, and cross-sectional areas of the individual filaments, and the electrical conductivity of the individual filaments. And of course, the design parameters may be different for each of the flexible filaments 12. Other design considerations may include, but are not limited to, the overall shape and cross-sectional area of the brush, the packing density of the flexible filaments 12 within the brush, and the overall electrical resistance of the brush.

The flexible filaments 12 together form what is referred to as a "working surface." The brush electrode 10 depicted in FIG. 1 has a relative flat working surface. In other words, all of the filaments 12 extend approximately the same distance from the distal end of the outer sheath 14 of the brush electrode 10. However, the flexible filaments 12 do not need to be perfectly aligned with one other longitudinally and may therefore form different shaped working surfaces, as may be desired for various procedures and/or for use on various tissue types.

When used for ablation procedures, the brush electrode 10 may be configured to deliver ablative energy to the tissue via conductive filaments, via a conductive fluid, or via a combination of conductive filaments and conductive fluid. Where a conductive fluid is used, the brush electrode 10 is referred to as a "wet-brush electrode." In a wet-brush electrode, the conductive fluid serves thermodynamic, mechanical, and electrical functions. Thermodynamically, the conductive fluid cools both the electrode and the electrode. Cooling of the tissue surface permits longer application of relatively high ablative energy. Mechanically, the flexible filaments 12 create a flexible working surface that provides improved tissue contact. The flexible filaments 12 also create interstitial spaces, which not only provide effective fluid channeling, but also prevent the ablative energy from being washed away by the surrounding blood, and helps to smooth the concentration gradient of the conductive fluid. Electrically, the conductive fluid serves as a "virtual electrode." The conductive fluid also insulates the flexible filaments 12 from the surrounding blood, which helps prevent the formulation of coagulum.

As mentioned above, the brush electrode 10 may also include one or more piezoelectric sensor 20 embedded among the filaments 12. In FIG. 1, the piezoelectric sensor 20 is embedded in the flexible filaments 12 so that it is substantially at the center of the brush electrode 10. However, such positioning is not required. The piezoelectric sensor 20 generates electric signals in response to stresses caused by contact with a surface (e.g., tissue).

In an exemplary embodiment, the piezoelectric sensor 20 may include a piezoelectric film 21 laminated within a flexible polymer 22 (e.g., plastic). The piezoelectric film 21 is about 28 μm thick, and is laminated on each side by about 0.1 mm of the flexible polymer 22. The flexible polymer protects the piezoelectric film 21 from external damage or corrosion, and provides electrical and/or thermal insulation. The flexible polymer 22 may also serve as a low pass mechanical filter. That is, the flexible polymer 22 attenuates high frequency "noise" signals caused, e.g., by minor vibrations from intermittent contact during positioning of the brush electrode 10 adjacent the tissue. Accordingly, high frequency noise signals are damped, or even non-existent, as output for the use.

Electrical wiring (not shown) may also be connected to the piezoelectric sensor 20. The electrical wiring may extend through the lumen of the brush electrode 10 to deliver electrical signals form the piezoelectric sensor 20 to a data acquisition/processing/output device (also not shown), such as, e.g., an echocardiogram (ECG) device. Alternatively, a wireless connection may be implemented, e.g., by providing a transmitter in the catheter and a receiver in association with the data acquisition/processing/output device.

In use, the piezoelectric sensor 20 responds to electrode-tissue contact stresses by generating electrical energy (e.g., a voltage). In FIG. 1a, it can be readily seen that piezoelectric sensor 20 is stressed or strained due to stress in the directions illustrated by arrows 18 (e.g., caused by movement over a tissue as illustrated in FIG. 3a-b). In other embodiments, the piezoelectric sensor 20 may include more than one layer of piezoelectric film 21. For example, a piezoelectric sensor 20 may be comprised of separate layers of piezoelectric film laminated on opposite sides of a central support structure (not shown). In still other embodiments, a twisted (e.g., quarter-twisted) piezoelectric sensor 20 may be provided to receive signals in bi-planar and full-arc multi-planar orientations.

In any event, the piezoelectric sensor 20 responds by generating electrical (voltage) signals. These electrical signals may be viewed by the user, e.g., as output on an electrical monitoring device. Accordingly, when the brush electrode 10 is positioned in contact with and/or moved over a tissue, the piezoelectric sensor 20 generates an electrical signal corresponding to stress caused by this contact and/or movement. The resulting electrical signal may be processed and/or otherwise output for the user so that the user is able to assess tissue contact by the brush electrode 10.

Piezoelectric sensors which generate electrical energy in response to applied mechanical stress are well-understood in the electro-mechanical arts. In general, piezoelectric sensors comprise a piezoelectric material which contains positive and negative electrical charges. In a neutral or "non-stressed" state, these electrical charges are symmetrically distributed in the piezoelectric material such that the material exhibits an overall neutral electrical charge. However, subjecting the piezoelectric material to a mechanical stress (e.g., flexure, pressure, and/or tension) disturbs the symmetrical distribution of electrical charges, thereby generating electrical energy across the material. Even minor deformation of some piezoelectric materials (e.g., on the order nanometers) may generate a measureable voltage signal. Operation of piezoelectric material may be better understood with brief reference to FIG. 2a-c.

Figure 2:
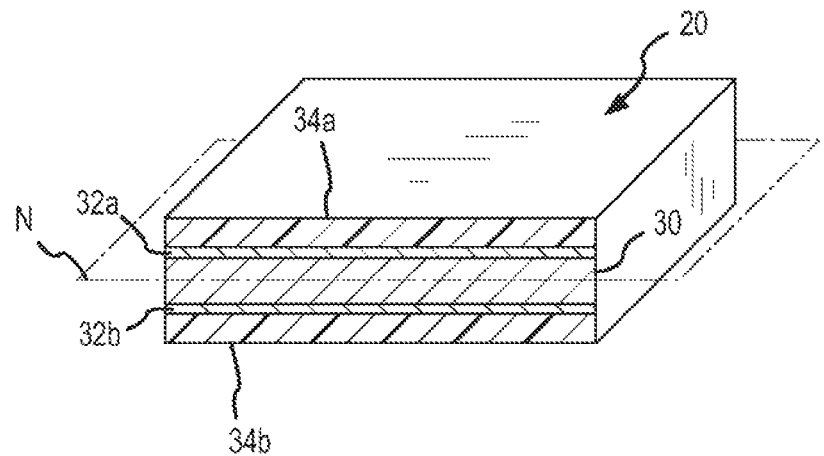
FIG. 2 is a cross-sectional perspective view of a portion of an exemplary piezoelectric sensor which may be implemented in the brush electrode.
Figure 2A:
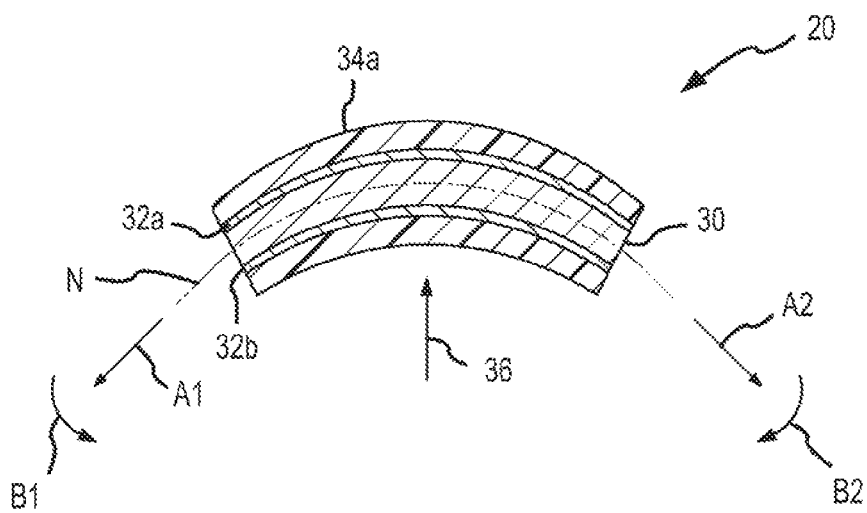
Figure 2B:
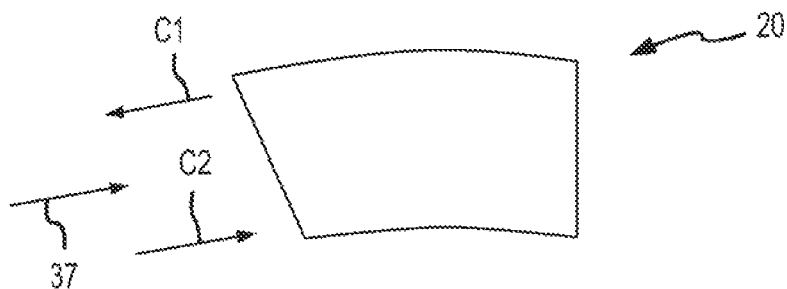

FIG. 2 is a cross-sectional perspective view of a portion of an exemplary piezoelectric sensor 20 which may be implemented in the brush electrode. In FIG. 2a-b, the piezoelectric sensor 20 is shown in exaggerated form as it may respond to various stresses, wherein FIG. 2a is a side-view of piezoelectric sensor 20 shown in FIG. 2, and FIG. 2b is a top-view of the piezoelectric sensor 20 shown in FIG. 2.

In an exemplary embodiment, the piezoelectric sensor 20 may be laminated sensor or film having a plurality of laminated layer. Although not required, laminated the sensor increases its sensitivity. Piezoelectric films are flexible, lightweight, and tough engineered plastic that is available in a wide variety of thickness and large area. Among other advantages, piezoelectric film has a low acoustic impedance which is close to that of water, human tissue, and other organic materials. For example, the acoustic impedance piezoelectric film is only about 2.6 times the acoustic impedance of water. Piezoelectric film also has a low density and excellent sensitivity, and is mechanically tough. When extruded into a thin film, piezoelectric polymers can be directly attached to a support structure without distributing its mechanical range of motion. Piezoelectric film is therefore well suited to strain-sensing application requiring very wide bandwidth and high sensitivity.

In FIG. 2, the laminated layers of piezoelectric sensor 20 may comprise a piezoelectric material 30 "sandwiched" between metal layers 32a and 32b and protective coating 34a and 34b. Metal layers 32a and 32b may be any suitable metal, e.g., a thin layer of silver ink. The metal layers 32a and 32b server to collect electrical charge generated by the piezoelectric material 30, e.g., for delivery as electrical signals via electrical wiring to a data acquisition/processing/output device. Metal layers 32a and 32b serve to collect electrical energy in response to stress of the piezoelectric material 30. Piezoelectric material, such as PVDF (Kynar), is commercially available as a highly-sensitive, thin, flexible polymer film, which makes it particularly desirable for use with deflectable catheters. Protective coating 34a and 34b may be any suitable material, e.g., Mylar®.

It is noted that the laminated layers of piezoelectric sensor 20 are not limited to any particular material and/or configuration. For example, the piezoelectric sensor 20 is not limited to use with separate metal layers 32a and 32b. Nor is the piezoelectric sensor 20 limited to the generally rectangular configuration shown in FIG. 2.

In an exemplary embodiment, the piezoelectric material 30 may comprise a thin, flexible, polymer-based material. One such piezoelectric film is a polyvinylidene fluoride (PVDF) film commercially available from the Sensor Products Division of Measurement Specialties, Inc. (Norristown, Pa.). This PVDF film is approximately 28 µm thick, enabling the PVDF film to be readily housed within the catheter shaft 14.

In addition, this PVDF film has a wide frequency range of bout 0.001 Hz to $10^9$ Hz and a high dynamic stress constant ($g_{31}=216\times10^{-3}$ Vm/N). For purposes of illustration, other common piezoelectric materials, such as lead zirconate titanate (PZT) has a dynamic stress constant ($g_{31}$) of $10\times10^{-3}$ Vm/N, and barium titanium oxide ($BaTiO_3$) has a dynamic stress constant ($g_{31}$) of $5\times10^{-3}$ Vm/N. Accordingly, the PVDF film is very sensitive, exhibiting a relatively high voltage response to relatively small mechanical stresses, and it therefore well-suited for measuring dynamic stresses and strains.

Of course the piezoelectric sensor 20 described above with reference to FIG. 2 is for purpose of illustration and not intended to be limiting. Other piezoelectric sensors may also be implemented, and are not limited to laminated piezoelectric film. Nor are piezoelectric sensors limited to use with any particular type or size of piezoelectric material. Selection of piezoelectric sensor 20 for use with the brush electrode 10 may be application-specific and depend at least in part on one or more design considerations, such as, but no limited to, the desired sensitivity and/or spatial constraints for housing the piezoelectric sensor.

Piezoelectric sensor 20 is shown in FIG. 2 in a neutral state. In the neutral state, the piezoelectric material 30 is not subject to any stresses or strains. Accordingly, the electrical charges are symmetrically distributed on either side of the neutral plane N in the piezoelectric material 30 such that the material exhibits an overall neutral electrical charge.

The most widely used coefficients, d3n (for charge) and g3n (for voltage), possess two subscripts. The first refers to the electrical axis, while the second subscript refers to the mechanical axis. Because piezoelectric film is thin, the electrodes are only applied to the top and bottom film surfaces. Accordingly, the electrical axis is always referred to as "3", as the charge or voltage is always transferred through the thickness (n=3) of the film, The mechanical axis can be either 1, 2, or 3, because the stress can be applied to any of these axes. Typically, piezoelectric film is used in the mechanical 1 direction for low frequency sensing and actuation (<100 KHz) and in the mechanical 3 direction for high ultrasound sensing and actuation (>100 KHz). These stresses can be better understood with reference to FIGS. 2a and 2b.

FIG. 2a is a side-view of the piezoelectric sensor 20 shown in FIG. 2. In FIG. 2a, the piezoelectric sensor 20 is shown in exaggerated form as it may respond to transverse stresses applied generally in the direction of arrow 36. In this stressed state, the piezoelectric material 30 undergoes transverse strain relative to its neutral state, as illustrated by arrows A1 and A2. The piezoelectric sensor 20 may also respond to bending stresses. In this stressed state, the piezoelectric material undergoes flexural strain relative to its neutral state, as illustrated by arrows B1 and B2.

FIG. 2b is a top-view of the piezoelectric sensor 20 in FIG. 2. In FIG. 2b, the piezoelectric sensor 20 is shown in exaggerated form as it may respond to longitudinal stresses applied generally in the direction of arrows 37a and 37b. In this stressed state, the piezoelectric material 30 is longitudinally strained relative to its neutral state, as illustrated by arrows C1 and C2.

Figure 3:
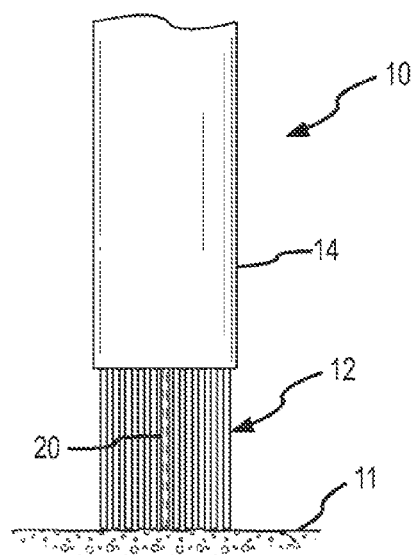
FIG. 3 is a side view showing the exemplary brush electrode FIG. 1 in a neutral state.
Figure 3A:
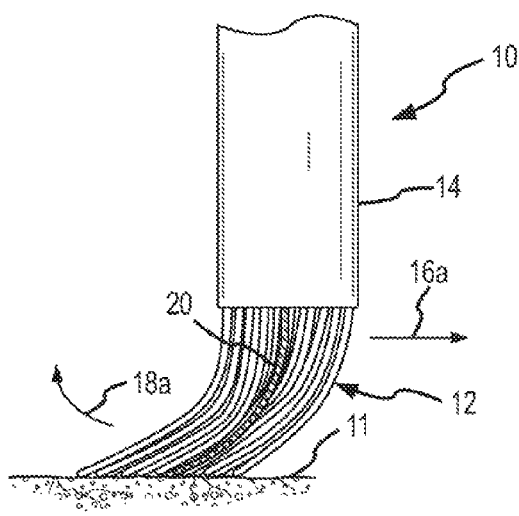
FIG. 3a and 3b show the brush electrode in operation as it may be moved along a tissue.
Figure 3B:
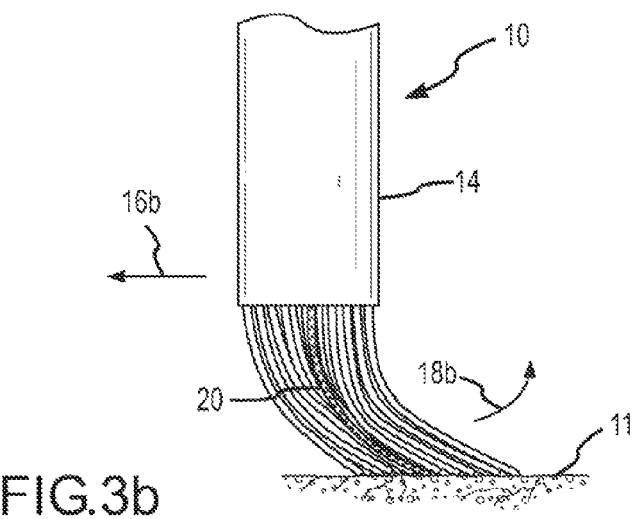

Turning to FIG. 3 and FIG. 3a-b, when the filaments 12 of brush electrode 10 are in a substantially neutral state (FIG. 3), the electrical charges are evenly distributed across the piezoelectric material (e.g., piezoelectric material 30 in FIG. 2). When the brush electrode 10 is moved over tissue 11 in direction 16a (illustrated by FIG. 3a) or in direction 16b (illustrated by FIG. 3b), the flexible filaments 12 and piezoelectric sensor 20 is deflected by the tissue 11 in direction 18a or direction 18b, respectively. Because the piezoelectric sensor 20 resides at the distal portion of the brush electrode 10 (and in this embodiment, the piezoelectric sensor 20 extends to the working surface of the brush), the piezoelectric sensor 20 responds directly and proportionally to the deflection of the filaments 12. Due to the intrinsic properties of piezoelectric material, the piezoelectric sensor 20 is a dynamic device and operates with continuous movement. This deflection disturbs the symmetrical distribution of electrical charges across the piezoelectric material, and electrical energy is generated. In operation, this electrical energy may be collected (e.g., by metal layers 32a, 32b in FIG. 2) and delivered as an electrical signal via electrical wiring through the catheter shaft to a data acquisition/processing/output device (not shown) for output to a user.

The signal strength (e.g., amplitude) from the piezoelectric sensor 20 is proportional to the amount of stress due to the tissue contact, and therefore can be used to assess tissue contact by the filaments 12 of brush electrode 10. If the contact is insufficient for the procedure, then there are no peaks in the output. On the other hand, a strong correlation between the heartbeat and output by the piezoelectric sensor 20 indicates sufficient or good tissue contact.

Signal periodicity is also a strong indicator of dynamic contact assessment. For example, if the period between heartbeats corresponds well with the period output by the piezoelectric sensor 20, stresses on the piezoelectric sensor 20 are being cause by the heartbeat (and not some other reason). According, the user may use this feedback to achieve the desired tissue contact.

It is noted that any suitable analog and/or digital device may be implemented for outputting the electrical signals generated by piezoelectric sensor 20 to a user. In addition, the electrical signals may be further characterized using a suitable processing device such as, but not limited to, a desktop or laptop computer. Such processing device may be implemented to receive the voltage signal generated by the piezoelectric sensor 20 and convert it to a corresponding contact condition and output for the user, e.g., at a display device, an audio signal, or tactile feedback or vibrations on the handle of the catheter. In any event, circuitry for conveying output of the piezoelectric sensor 20 to a user in one form or another may be readily provided by those having ordinary skill in the electronics arts after becoming familiar with the teachings herein.

Figure 4:
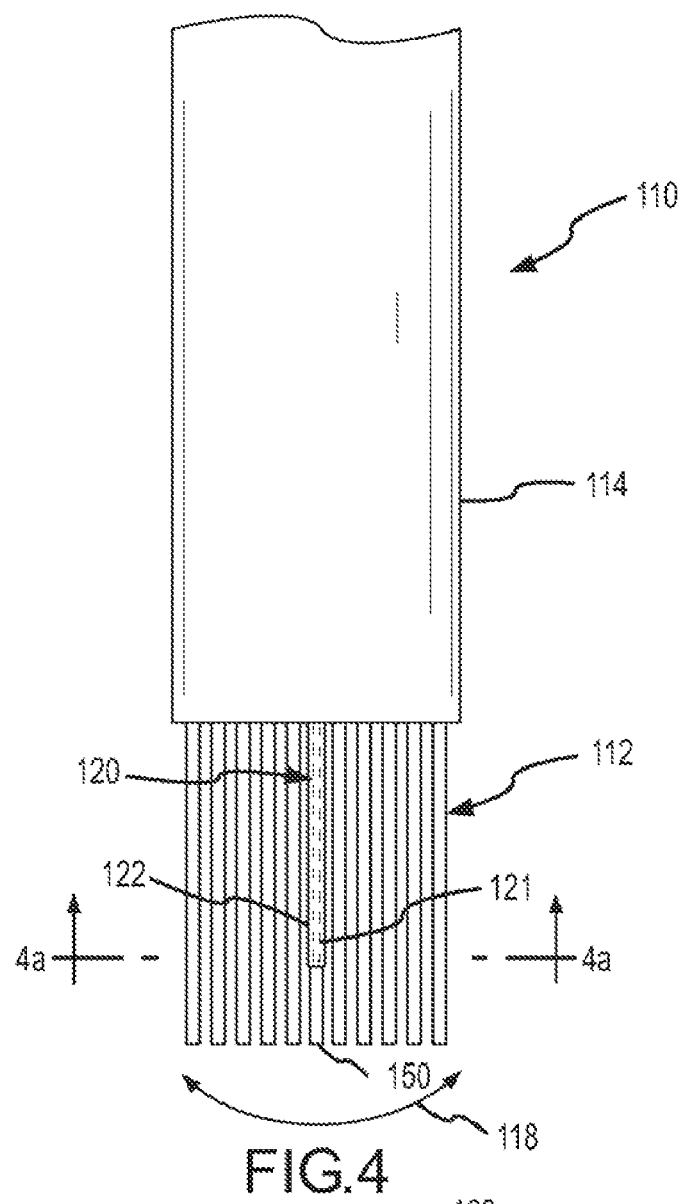
FIG. 4 is a side view of another exemplary embodiment of a brush electrode according to the present invention.
Figure 4A:
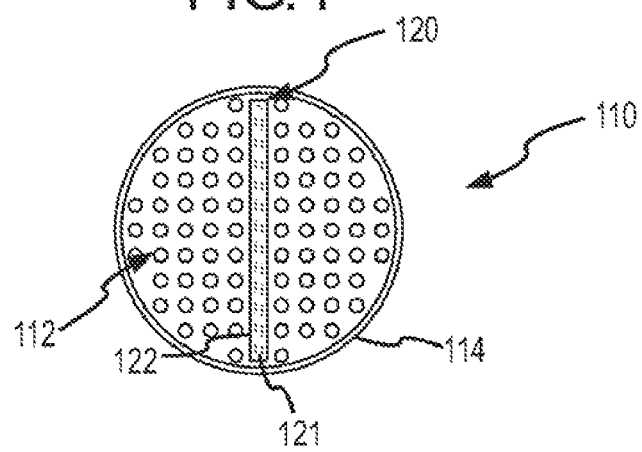
FIG. 4a is a cross-sectional view of the brush electrode taken along lines 4a-4a in FIG. 4.
Figure 5:
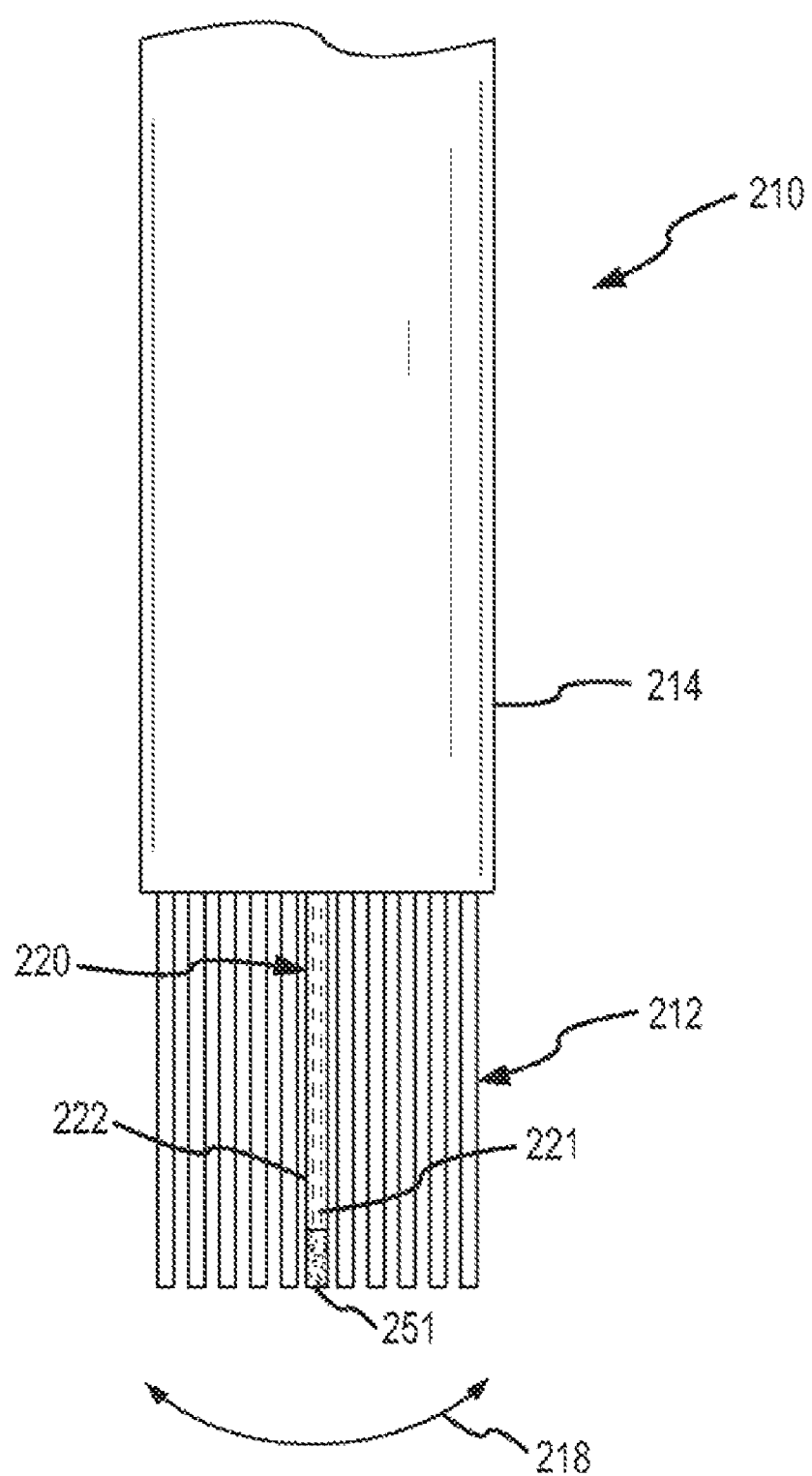
FIG. 5 is a side view of another exemplary embodiment of a brush electrode.

FIG. 4 is a side view of another exemplary embodiment of a brush electrode 110 according to the present invention. FIG. 4a is a cross-sectional view of the brush electrode 110 taken along lines 4a-4a in FIG. 4. FIG. 5 is a side view of another exemplary embodiment of a brush electrode 210. It is noted that 100-series reference number are used in the embodiment shown in FIGS. 4 and 4a to refer to like elements described above with reference to FIGS. 1 and 1a-b. Therefore the description of some elements may not be repeated in the following discussion.

In the embodiment depicted in FIGS. 4 and 4a, the piezoelectric sensor 120 to the working surface of the brush. The filament portion 150 serves to deflect the piezoelectric sensor 120 when in contact with and/or moved along a tissue (e.g., as shown in FIG. 3a-b).

This configuration serves to isolate the piezoelectric sensor 120 from direct contact with the tissue, and may be used where power, blood flow, and/or irrigation conditions cause the working surface of the brush electrode 110 to reach high temperatures which can change the sensitivity of the piezoelectric sensor 120. In these situations, the temperature is typically as the distance from the tissue increases, e.g., where the piezoelectric sensor 120 is shown in FIGS. 4 and 4a. Accordingly, the piezoelectric sensor 120 may better maintain the desired sensitivity to deflection for sensing operations.

This configuration may also be used to provide secondary sensors at the working surface of the brush electrode. FIG. 5 is a side view of another exemplary embodiment of a brush electrode 210. It is noted that 200-series reference numbers are used in the embodiment shown in FIG. 5 to refer to like elements described above with reference to FIGS. 1 and 1a-b. Therefore the description of some elements may not be repeated with reference to FIG. 5. For example, various sensing devices 251 (e.g., pressure, thermistor, thermocouple, or ultrasound sensors) may be provided in series with the piezoelectric sensor 220 to provide additional feedback to the user.

Figure 6:
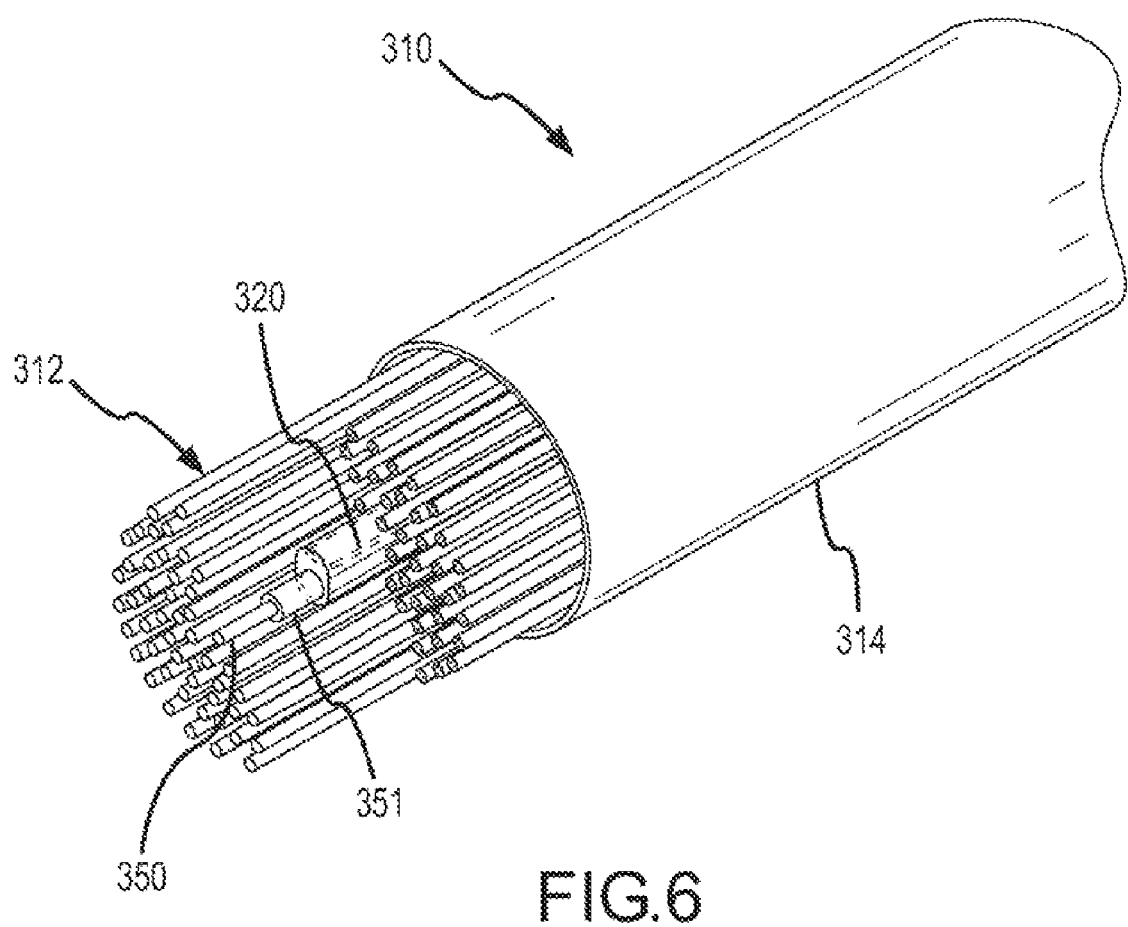
FIG. 6 is a perspective view of another exemplary embodiment of a brush electrode having a plurality of flexible filaments, and depicts a piezoelectric sensor and a sensing device embedded among the flexible filaments.
Figure 6B:
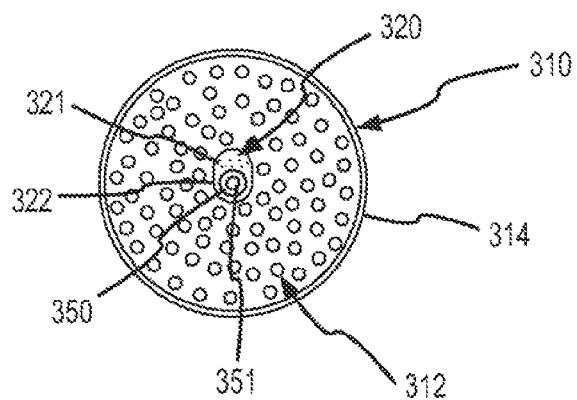
Figure 6A:
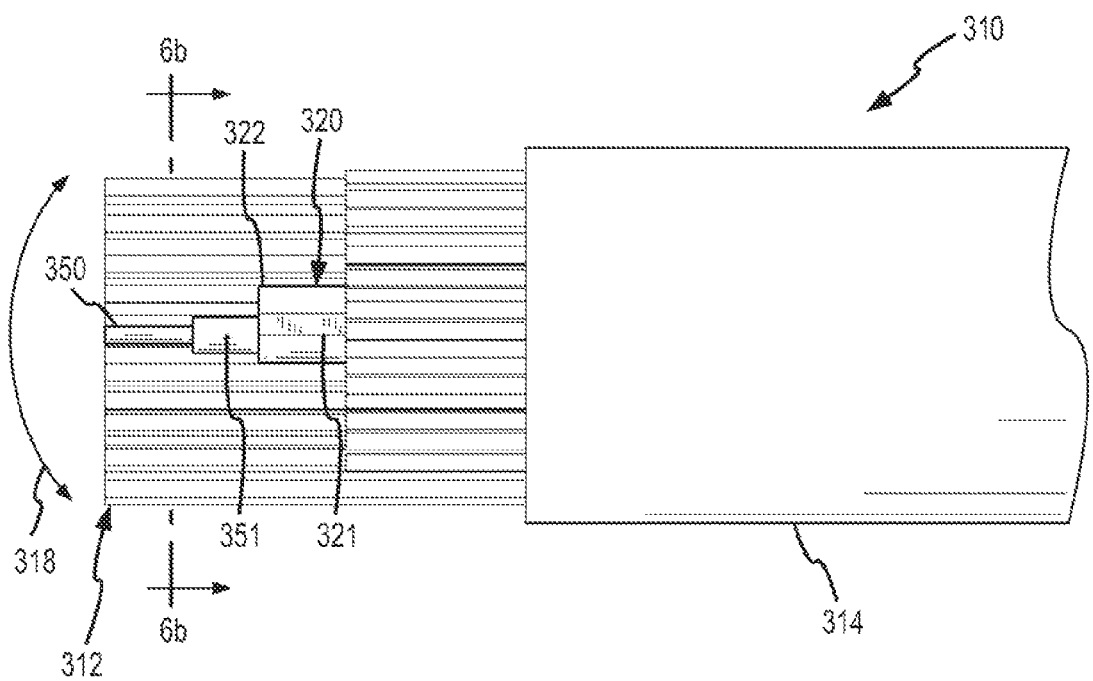
FIG. 6a is a side view of the brush electrode shown in FIG. 6.

It is noted that these sensing devices are not limited to being provided in series with the piezoelectric sensor. Other embodiments are also contemplated. For example. FIG. 6 is a perspective view of another exemplary embodiment of a brush electrode 310 having a plurality of flexible filaments 312, and depicts a piezoelectric sensor 320 and a sensing device 351 embedded among the flexible filaments 312. FIG. 6a is a side view of the brush electrode 310 shown in FIG. 6. FIG. 6b is a cross-sectional view of the brush electrode 310 taken along lines 6b-6b in FIG. 6a. It is noted that 300-series reference numbers are used in the embodiment shown in FIGS. 6 and 6a-b to refer to like elements described above with reference to FIGS. 1 and 1a-b. Therefore the description of some elements may not be repeated in the following discussion.

In the embodiment depicted in FIGS. 6 and 6a-b, the piezoelectric sensor 320 and sensing device 351 are provided adjacent one another and extend beyond the sheath 314 for a distance that is shorter than that of the filaments 312. A filament portion 350 extends in series from the piezoelectric sensor 320 and sensing device 351 to the working surface of the brush. The filament portion 350 serves to deflect the piezoelectric sensor 320 when in contact with and/or moved along a tissue (e.g., as shown in FIG. 3a-b).

This configuration serves to isolate the piezoelectric sensor 320 and sensing device 351 from direct contact with the tissue, and as discussed above with reference to FIG. 4, may be used where power, blood flow, and/or irrigation conditions cause the working surface of the brush electrode 310 to reach high temperatures.

Although the filaments of the brush electrode can bend in any direction and the piezoelectric sensor still generates a signal, the piezoelectric sensor is not as sensitive in multiple directions. That is, the piezoelectric sensor is most sensitive if it is positioned or moved in a uni-planar direction from the position where the flat surface of the piezoelectric sensor is facing (e.g., as illustrated in FIG. 3a-b).

Figure 7:
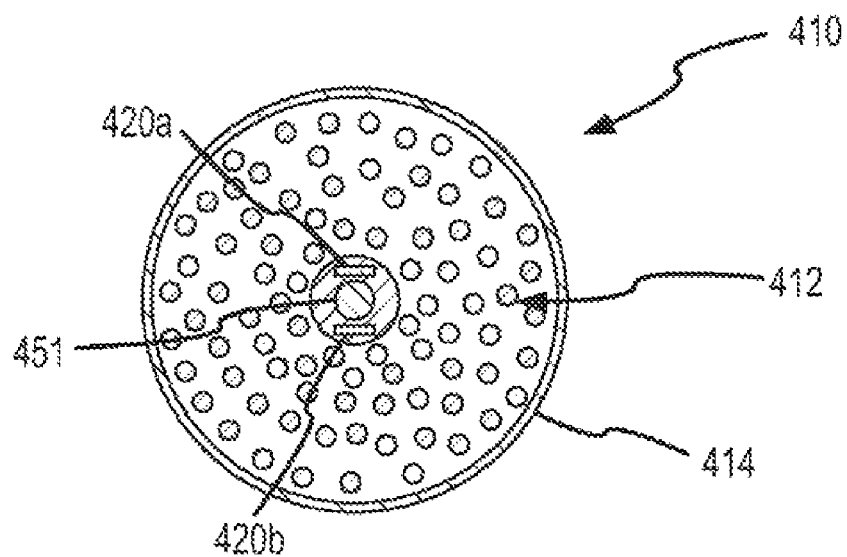
FIG. 7 and 8 are cross-sectional views of alternative embodiments for embedding the piezoelectric sensor and secondary sensing device in the brush electrode shown in FIG. 6.
Figure 8:
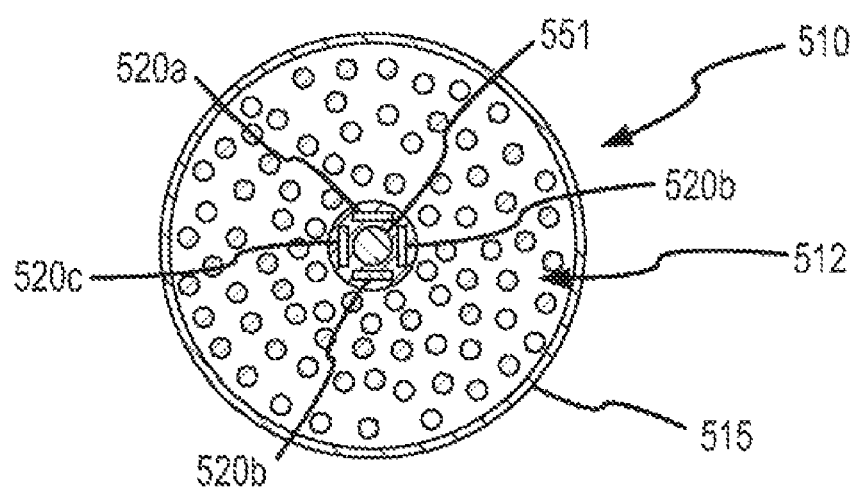

To receive a signal from other directions of movement, multiple piezoelectric sensors may be embedded among the filaments in the brush electrode. FIGS. 7 and 8 are cross-sectional views of alternative embodiments of brush electrodes 410 and 510 with multiple piezoelectric sensors 420a-b and 520a-d, respectively. It is noted that 400- series reference numbers are used in the embodiment shown in FIG. 7, and that 500-series reference numbers are used in the embodiment shown in FIG. 8, to refer to like elements described above with reference to FIGS. 1 and 1a-b. Therefore the description of some elements may not be repeated with reference to FIGS. 7 and 8.

In FIG. 7, two piezoelectric sensors 420a-b are shown on opposite sides of the sensing device 451, and in FIG. 8, four piezoelectric sensors 520a-d are shown on each side of the sensing device 551. Signals from the multiple piezoelectric sensors may be combined to improve sensitivity of the contact sensing. Additionally, because the stress response of piezoelectric materials is anisotropic, the different orientation of piezoelectric sensors 520a-b relative to 520c-d may be used to attenuate directional differences and are used to provide directional information of the tissues contact.

Although several embodiments of this invention have been described above with a certain degree of particularly, those skilled in the art could make numerous alterations to the disclosed embodiments without departing from the spirit or scope of this invention. References are only used for identification purposes to aid the reader's understanding of the present invention, and do not create limitations as to the position, orientation, or use of the invention. In addition, various combinations of the embodiments shown are also contemplated even if not particularly described. Changes in detail or structure, such as but not limited to combinations of various aspects of the disclosed embodiments, may be made without departing from the spirit of the invention as defined in the appended claims.

What is claimed is:

1. A brush electrode for tissue contact assessment comprising:
    a plurality of flexible filaments adapted to transfer electrical energy to tissue;

at least one piezoelectric sensor embedded among the plurality of flexible filaments, the at least one piezoelectric sensor extends beyond a sheath but for a shorter distance than the flexible filaments to isolate the at least one piezoelectric sensor from direct contact with the tissue, the at least one piezoelectric sensor responsive to contact stress of the flexible filaments by generating electrical signals corresponding to the amount of contact stress.

2. The brush electrode of claim 1, wherein the tissue contact is proportional to the signal strength.

3. The brush electrode of claim 1, wherein the tissue contact is proportional to amplitude of the electrical signals.

4. The brush electrode of claim 1, wherein the tissue contact corresponds to periodicity of the electrical signals.

5. The brush electrode of claim 1, wherein the at least one piezoelectric sensor includes a laminated piezoelectric film.

6. The brush electrode of claim 1, wherein a plurality of separate piezoelectric sensors are provided for outputting directional information of the tissue contact.

7. The brush electrode of claim 1, wherein the at least one piezoelectric sensor extends substantially the same distance as the flexible filaments.

8. The brush electrode of claim 1, further comprising a sensing device mounted adjacent the at least one piezoelectric sensor.

9. The brush electrode of claim 8, wherein the sensing device is a pressure sensor, a thermistor, a thermocouple, or an ultrasound sensor.

10. The brush electrode of claim 1, wherein the brush electrode further includes interstitial spaces adapted to convey a conductive fluid to a tissue.

11. A method for assessing tissue contact based on piezoelectric signals, comprising providing an exposed portion of a brush electrode for positioning adjacent to a tissue;

generating piezoelectric signals in response to stress caused by a exposed portion of the brush electrode contacting the tissue; and detecting stress due to movement of the brush electrode in any direction using a twisted piezoelectric sensor.

12. The method of claim 11, further comprising generating output corresponding to a condition detected at the exposed portion of the brush electrode.

13. The method of claim 12, wherein the condition detected at the exposed portion of the brush electrode is temperature.

14. The method of claim 11, wherein assessing the tissue contact is based at least in part on strength of the piezoelectric signals.

15. The method of claim 11, wherein assessing the tissue contact is based at least in part on amplitude of the piezoelectric signals.

16. The method of claim 11, wherein assessing the tissue contact is based at least in part on periodicity of the piezoelectric signals.

17. The method of claim 11, further comprising reducing noise artifacts during movement of the brush electrode.

18. The method of claim 11, further comprising reducing noise effects from intermittent contact of the brush electrode.

19. The method of claim 11, further comprising determining direction and plane of the tissue contact based at least in part on relative magnitude and direction of signals obtained from each of at least two piezoelectric sensors.

20. A system comprising:

conforming means for transferring electrical energy to tissue;

means for generating piezoelectric signals corresponding to contact stress of the conforming means, the means for generating piezoelectric signals extending beyond a sheath but for a shorter distance than the conforming means to isolate the means for generating piezoelectric signals from direct contact with the tissue; and means for assessing tissue contact of the conforming means based at least in part on the piezoelectric signals.

21. The system of claim 20, further comprising sensor means for generating output corresponding to a condition detected near the conforming means.

* * * * *